(12) United States Patent
Rusu et al.

(10) Patent No.: US 9,852,501 B2
(45) Date of Patent: Dec. 26, 2017

(54) TEXTURAL ANALYSIS OF DIFFUSED DISEASE IN THE LUNG

(71) Applicant: GENERAL ELECTRIC COMPANY, Schenectady, NY (US)

(72) Inventors: Mirabela Rusu, Malta, NY (US); Roshni Bhagalia, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 26 days.

(21) Appl. No.: 15/161,679

(22) Filed: May 23, 2016

(65) Prior Publication Data

US 2017/0337676 A1 Nov. 23, 2017

(51) Int. Cl.
| | | |
|---|---|---|
| G06K 9/00 | (2006.01) | |
| G06T 7/00 | (2017.01) | |
| G06K 9/62 | (2006.01) | |
| A61B 6/03 | (2006.01) | |
| A61B 6/00 | (2006.01) | |

(52) U.S. Cl.
CPC ............ *G06T 7/0008* (2013.01); *A61B 6/032* (2013.01); *A61B 6/50* (2013.01); *G06K 9/628* (2013.01); *G06K 9/6228* (2013.01); *G06T 7/001* (2013.01); *G06T 2207/10081* (2013.01); *G06T 2207/20076* (2013.01); *G06T 2207/20081* (2013.01); *G06T 2207/30061* (2013.01)

(58) Field of Classification Search
None
See application file for complete search history.

(56) References Cited

U.S. PATENT DOCUMENTS

| | | |
|---|---|---|
| 6,466,687 B1 | 10/2002 | Uppaluri et al. |
| 8,811,724 B2 | 8/2014 | Nielsen et al. |
| 2010/0260396 A1 | 10/2010 | Brandt et al. |
| 2013/0129168 A1 | 5/2013 | Ross |
| 2013/0338489 A1 | 12/2013 | Prisk et al. |
| 2014/0184608 A1 | 7/2014 | Robb et al. |

(Continued)

FOREIGN PATENT DOCUMENTS

CN 201400196 Y 2/2010

OTHER PUBLICATIONS

Huber, et al; "Classification of Interstitial Lung Disease Patterns with Topological Texture Features," Item Title, May 27, 2010, pp. 1-8.

(Continued)

*Primary Examiner* — Atiba O Fitzpatrick
(74) *Attorney, Agent, or Firm* — Pabitra K. Chakrabarti

(57) ABSTRACT

A method of creating a diagnostic evaluation for usual interstitial pneumonia is provided, including obtaining a first plurality of series of HRCT lung slices indicating the presence of UIP, obtaining an identification of UIP and non-UIP voxels, extracting textural and localization features from the UIP and non-UIP voxels, selecting features that are more accurate in differentiating UIP voxels from non-UIP voxels than other features are, eliminating features highly correlated with a more accurate feature, and constructing a predictive model by performing a second classifier to provide a probability that a voxel signifies the presence of UIP. Also provided is a method of identifying UIP in a subject's lung by applying a diagnostic evaluation for UIP that was created with the foregoing method.

20 Claims, 8 Drawing Sheets

(56) References Cited

U.S. PATENT DOCUMENTS

2015/0254843 A1 9/2015 Brown et al.
2016/0260224 A1* 9/2016 Ward .................... G06T 7/0012

OTHER PUBLICATIONS

Caban, et al; "Texture-based computer-aided diagnosis system for lung fibrosis," Prov. SPIE 6514, Medical Imaging 2007: Computer-Aided Diagnosis, Mar. 30, 2007, vol. 6514.

Karasawa, et al; "Determination of lung regions on chest ct images with diffuse lung diseases by use of anatomical structures and pulmonary textures," Conf. Proc IEEE End. Med. Biol. Soc., Aug. 2015, pp. 2985-2988.

* cited by examiner

TEXTURAL ANALYSIS OF DIFFUSED DISEASE IN THE LUNG

FIELD

The invention relates generally to using textural and localization features for identifying diffused disease in the lung.

BACKGROUND

High-resolution computed tomography (HRCT) imaging of diffuse abnormalities in the lung plays an important role in the non-invasive disease management. However many interstitial lung diseases (ILDs) manifest similarly on HRCT making it difficult to reliably distinguish between them without further processing. This results in false alarms, missed idiopathic lung fibrosis (IPF) diagnoses and unnecessary invasive procedures that can have a detrimental impact on a patient's quality of life. Several approaches have been introduced to automatically detect patterns associated with multiple ILDs. Others find patterns that distinguish usual interstitial pneumonia (UIP) versus normal tissue only, IPF versus normal or emphysematous tissue only, or differentiate between subtypes of UIP. While detecting such patterns is vital to improving HRCT-based disease diagnosis, each pattern can be indicative of more than one ILD with widely varying prognosis. Thus, to be clinically meaningful there is a need to develop an automated system that can differentiate between UIP and "non-UIP" tissue regions, including normal and other interstitial lung diseases with possibly better prognosis.

SUMMARY

In one embodiment, a method for creating a diagnostic evaluation for usual interstitial pneumonia (UIP) is provided. The method includes obtaining a first plurality of series of high resolution computed tomography (HRCT) slices of a plurality of subjects' lungs wherein some voxels of some of the first plurality of series indicate the presence of UIP; obtaining an identification of UIP voxels in at least some of the plurality of series and an identification of non-UIP voxels in at least some of the plurality of series wherein the UIP voxels represent the presence of UIP in an area of the lung represented by the UIP voxels and non-UIP voxels represent the absence of UIP in an area of the lung represented by the non-UIP voxels; extracting a first plurality of features from said UIP voxels and said non-UIP voxels, wherein extracting comprises measuring each of the first plurality of features as exhibited by the UIP voxels and by the non-UIP voxels and the first plurality of features includes first-order statistics, second-order statistics, gray level co-occurrence matrix, gray level run-length matrix, and location features; selecting features wherein selecting comprises performing a first classifier to obtain a rank of importance for each of the plurality of features in which a higher-ranked feature provides a measure that is more accurate in differentiating UIP voxels from non-UIP voxels than is a lower-ranked feature, and eliminating one or more redundant features wherein a redundant feature comprises a feature whose measure as exhibited by voxels is highly correlated with the measure of another feature as exhibited by voxels having a higher rank of importance than the redundant feature; and constructing a predictive model wherein constructing includes obtaining a second plurality of series of HRCT slices of subjects' lungs wherein some voxels of some of the plurality of series indicate the presence of UIP and training a number of the subset of features to provide a probability that a voxel signifies the presence of UIP by performing a second classifier on the number of the subset of features.

In another embodiment, a method for identifying the presence of UIP in a subject's lung is provided. The method includes obtaining a method for creating a diagnostic evaluation for usual interstitial pneumonia (UIP) as described above; obtaining a series of HRCT slices of the lungs of a subject; and measuring, for voxels of the series, each of the number of the subset of features to provide a probability that a voxel signifies the presence of UIP.

DRAWINGS

These and other features, aspects, and advantages of the present invention will become better understood when the following detailed description is read with reference to the accompanying drawings, wherein.

DETAILED DESCRIPTION

Figure 1:
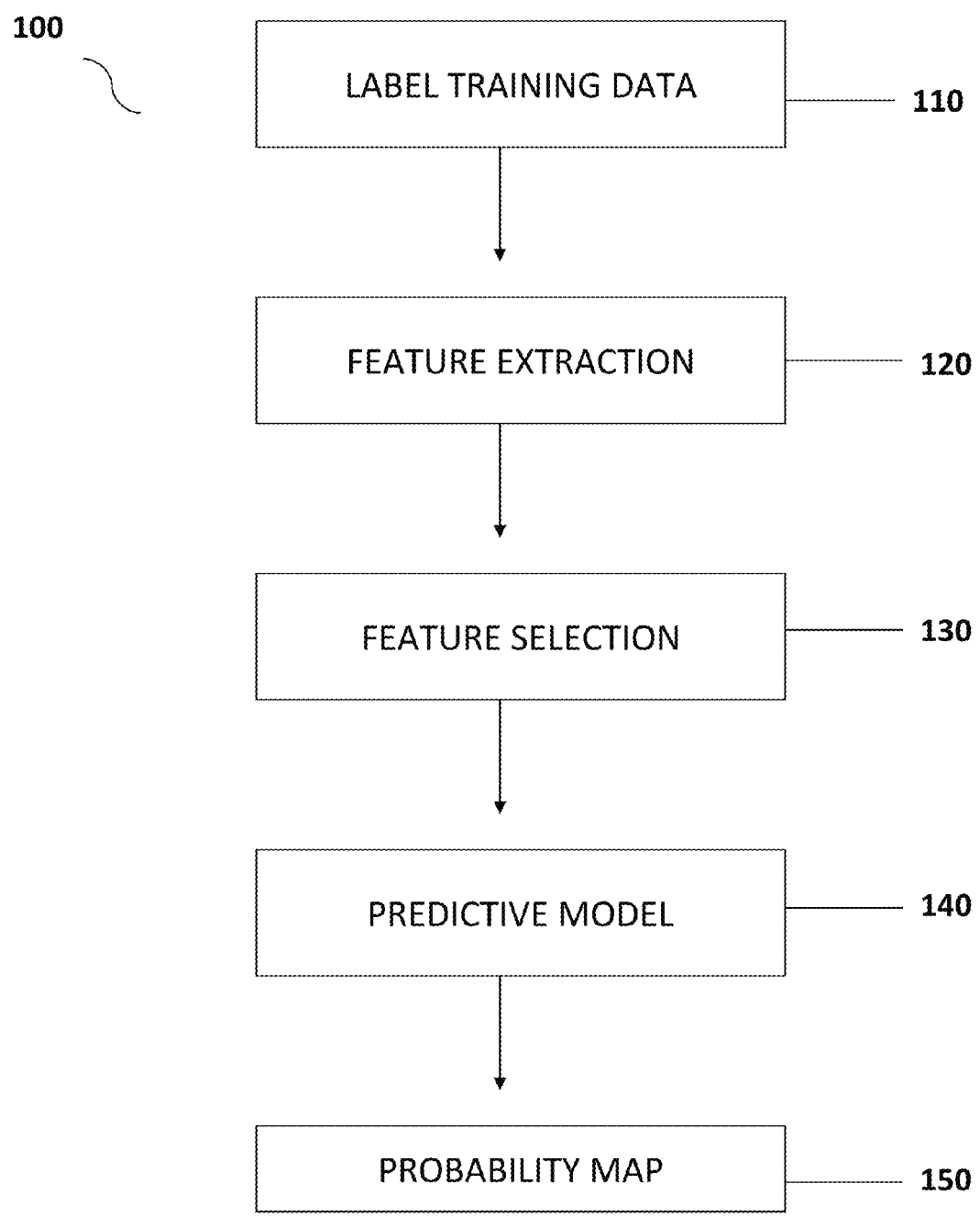
FIG. 1 is a flow-chart illustrating one example of a method for creating a diagnostic evaluation for UIP in accordance with the present invention.

In one aspect, an embodiment of the present invention includes a method of using a localization and textural features of UIP exhibited by HRCT scans of subjects' lungs to create a diagnostic evaluation for UIP. A method may include extracting a plurality of features from HRCT scans, selecting features that have a high rank of importance in predicting UIP, and constructing a predictive model for determining whether an HRCT lung scan indicates the possible presence of UIP tissue. In another aspect, an embodiment of the present invention includes obtaining a diagnostic evaluation for UIP using localization and textural features of UIP and using the method to determine a probability that an HRCT scan of a subject's lung indicates the presence of UIP.

In the following description and the claims that follow, whenever a particular aspect or feature of an embodiment of the invention is said to include, comprise, or consist of at least one element of a group and combinations thereof, it is understood that the aspect or feature may include, comprise, or consist of any of the elements of the group, either individually or in combination with any of the other elements of that group. Similarly, the singular forms "a", "an" and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "about" may not be limited to the precise value specified, and may include values that differ from the specified value. In at least some instances, the approximating language may correspond to the precision of an instrument for measuring the value. In the present discussions it is to be understood that, unless explicitly stated otherwise, any range of numbers stated during a discussion of any region within, or physical characteristic of, is inclusive of the stated end points of the range.

Many ILDs manifest similarly on HRCT making it difficult to reliably distinguish between them without further processing, which may result in false positives or false negatives. Disclosed herein are methods to detect IPF through detection of UIP using HRCT. UIP may presents on HRCT as a predominantly basal disease in the diaphragm with a typical honeycomb and reticular abnormalities appearance. Consequently, accurate detection of UIP on baseline HRCT is a direct predictor of IPF mortality and can be used to enable reliable, patient-specific disease management. Detecting patterns of features in HRCT lung scans may help identify UIP. In some instances, a pattern may be indicative of more than one ILD with widely varying prognosis. Hypersensitivity pneumonitis (HP) without fibrosis and IPF can manifest as honeycombing in HRCT. However HP patients may have an over 3 times longer median survival than patients with IPF and in turn the optimal management path for the two diseases is very different.

The present disclosure includes an automated system for differentiating between UIP regions and regions of tissue not characteristic of UIP, or non-UIP tissue regions, including non-disease and other interstitial lung diseases with possibly different prognoses. As disclosed herein, UIP may be distinguished from other non-UIP conditions upon analysis of an HRCT scan on a voxel-by-voxel basis. A dense set of local texture features in combination with spatial information may be identified, features selected to retain a parsimonious subset of informative features that are minimally inter-dependent, and a robust classifier may be trained and evaluated to predict presence of UIP on HRCT with high voxel-wise accuracy.

One non-limiting example of an embodiment disclosed herein whereby a method for creating a diagnostic evaluation for UIP 100 is shown in FIG. 1. In one aspect, a series of HRCT scans may be obtained of subjects confirmed by independent evaluation to exhibit UIP. Areas of scans indicative of UIP, referred to herein generally as UIP voxels, may be labeled 110, such as by a radiologist or other trained medical health care professional, and distinguished from other portions of scans that do not indicate UIP, referred to herein as non-UIP voxels. In another example, UIP and non-UIP voxels may be labeled 110 following a process of automated segmentation of HRCT scans between voxels indicative of each kind of tissue. An identifier of a voxel as a UIP voxel or non-UIP voxel may be incorporated in a computer-readable medium in which the HRCT image itself is stored as a distinguishing characteristic of each such voxel associated with other information thereof such as textural features or localization features the voxel also represents.

Features of UIP and non-UIP voxels may then be extracted 120 from labeled scans. UIP has a heterogeneous appearance on HRCT, e.g. honeycombing, reticular abnormalities or bronchiectasis which may be identified as textural features of HRCT scans. See Raghu et al., (2011), Am. J. of Respir. Crit. Care Med. 183:788-824. Such features tend to be non-uniformly distributed within the lung. Thus, a per-voxel prediction in accordance with the present invention may be more appropriate than strictly regional prediction. UIP is also characterized by predominantly plural and basal localization of disease. Disclosed herein is a method of integrating both local texture features derived from HRCT as well as localization features that quantify the spatial distribution of diseased tissue with respect to lung anatomy. To capture the spatially non-uniform distribution of UIP, voxel-wise predictions of the probability of UIP versus non-UIP may be obtained.

Textural features may include first order statistics, second order statistics, Haralick features extracted from co-occurrence matrices, and gray level run length. Such features are recognized in the field for potential in identifying diseased lung tissue, including UIP, and methods for extraction of specific individual types of such features from scans of lung tissue may be accomplished by well-known methods understood by skilled artisans in the relevant field. See Raghu et al., (2011), Am. J. of Respir. Crit. Care Med. 183:788-824; Galloway (1975), Comput. Gr. Image Process. 4:172-179; Haralick et al. (1973), IEEE Trans. Systems, Man and Cybern. 6:610-621; Russ, J. C.: The image processing handbook. CRC press (2015); Danielsson (1980), Computer Graphics and Image Processing, 14:227-248. Other textural features indicative of UIP are also well-known in the relevant field and may also be extracted in accordance with the present invention according to well-known methods. See Caban et al. (2007), Texture-based computer-aided diagnosis system for lung fibrosis, In: Proceeding, SPIE Med. Imaging. pp. 651439-651439; Delorme et al. (1997), Invest. Radiol. 32:566-574; Depeursinge et al. (2008), Lung tissue analysis using isotropic polyharmonic B-spline wavelets, MICCAI 08: Proceedings of the First International Workshop on Pulmonary Image Analysis, pp. 125-133; Song et al. (2013), IEEE, Trans. Med. Imaging 32:797-808; Yoon (2013), Euro. Radiol. 23:692-701.

In accordance with one embodiment of a method disclosed herein, value of textural features at each voxel of an HRCT scan may be computed within a sliding window $W_n(m)$ as defined herein. C may represent 3D volume defined by a CT scan. $C_{ijk}$ may represent a voxel in C, where i=1 ... N, j=1 ... M, k=1 ... O. $W_{i'j'k'}$ may represent a sliding window of radius $N_w$, $M_w$, $K_w$ surrounding voxel i,j,k, i'=i−$N_w$ ... i+$N_w$; j'=j−$M_w$ ... j+$M_w$; and k'=k−$O_w$ ... k+$O_w$. For simplification, each voxel $C_{ijk}$ may be denoted as C(n), n=1 ... K, with K=N*M*O, and the voxels in $W_{i'j'k'}$ be denoted by $W_n(m)$, with m=1 ... w, where w=(2Nw+1)*(2Mw+1)*(2Ow+1).

First-order statistics describe the distribution of CT intensities using basic measures defined relative to a simplified notation. Non-limiting examples of first-order statistics may include a mean, a median, a standard deviation, an energy, a skewness, an intensity, a root mean square a deviation, a uniformity, a maximum, a range, a minimum, an entropy, a mean absolute deviation, a variance, and a kurtosis. Computation of such features may be accomplished according to methodology well-recognized by those with skill in the relevant field.

For example, Median(n) may equal median of all voxels Wn(m).

Mean may be determined according to the following equation 1:

$$\overline{W(n)} = \frac{1}{w}\sum_{m=1}^{w} W_n(m) \qquad \text{Eq. 1}$$

Standard deviation may be determined according to the following equation 2:

$$\sigma(n) = \sqrt{\frac{1}{w-1}\sum_{m=1}^{w}(W_n(m)-\overline{W(n)})^2} \qquad \text{Eq. 2}$$

Energy may be determined according to the following equation 3:

$$\text{energy}(n) = \sum_{m=1}^{w} W_n^2(m) \qquad \text{Eq. 3}$$

Skewness may be determined according to the following equation 4:

$$\text{skewness}(n) = \frac{\frac{1}{w}\sum_{m=1}^{w}(W_n(m)-\overline{W(n)})^3}{\left(\sqrt{\frac{1}{w}\sum_{m=1}^{w}(W_n(m)-\overline{W(n)})^2}\right)^3} \qquad \text{Eq. 4}$$

Coefficient of variation may be determined according to the following equation 5:

$$\text{coef\_var}(n) = \sigma(n)/\overline{W(n)} \qquad \text{Eq. 5}$$

Second order statistics, which may be computed for each voxel $C_{ijk}$, represent statistical measures of gradients in an HRCT image. Non-limiting examples of second-order statistics may include a gradient z, a gradient y, a gradient x, a gradient magnitude, a gradient magnitude mean, a gradient magnitude standard deviation, a gradient magnitude skewness, a gradient magnitude kurtosis, and a gradient magnitude coefficient of variation. Computation of such features may be accomplished according to methodology well-recognized by those with skill in the relevant field.

For example, gradients may be determined according to the following equation 6:

$$\frac{dC}{dx} = \frac{C_{ijk} - C_{(i-1)jk}}{s_i} \qquad \text{Eq. 6}$$

$$\frac{dC}{dy} = \frac{C_{ijk} - C_{(j-1)k}}{s_j}$$

Gradient magnitude may be determined according to the following equation 7:

$$dC = \sqrt{\left(\frac{dC}{dx}\right)^2 + \left(\frac{dC}{dy}\right)^2} \qquad \text{Eq. 7}$$

Gray level co-occurrence features, also known as Haralick textural features, may be computed by first evaluating a co-occurrence matrix and then computing various metrics based on the co-occurrence matrix. The gray level co-occurrence matrix is defined as $P(i,j,\delta,\alpha)$ and has $N_G \times N_G$ elements, where $N_G$ represents discrete gray level intensities. $P(i,j)$ represents the number of times a combination of intensity level i and j occur in two pixels in an image that are separated by a distance of $\delta=1$ in the direction indicated by $\alpha=4$ and with a 2D computation due to the large spacing between slices. $P(i,j)$ represents an element in the co-occurrence matrix for any arbitrary $\delta$ and $\alpha$, according to the following equation 8:

$$p_{x-y}(k) = \sum_{i=1}^{N_g}\sum_{j=1}^{N_g} P(i,j), |i-j|=k, k=0,1,\ldots,N_g-1 \qquad \text{Eq. 8}$$

Nonlimiting aspects of Haralick textural features include an angular second moment, a contrast, a correlation, a sum of squares, a variance, an inverse difference moment, a sum average, a sum variance, a sum entropy, a entropy, a difference variance, a difference entropy, an information measure of correlation 1, and an information measure of correlation 2. Computation of such features may be accomplished according to methodology well-recognized by those with skill in the relevant field.

For example, angular second moment may be determined according to the following equation 9:

$$f_1 = \sum_i \sum_j P(i,j)^2 \qquad \text{Eq. 9}$$

Difference variance may be determined according to the following equation 10:

$$f_{10} = \text{variance of } p_{x-y} \qquad \text{Eq. 10}$$

As would be recognized by skilled artisans on the basis of published literature, gray-level run-length based features evaluate statistics over gray level runs in an HRCT image. See Galloway (1975), Computer Graphics and Image Processing, 4:172-179. A gray level run is defined as the length (number of pixels) of consecutive pixels that have the same gray-level value. In a gray level run length matrix, $p(i,j|\theta)$ may describe the number of times j a gray level i appears consecutively in the direction specified by $\theta$. $N_g$ is the number of discrete intensity values, while $N_r$ is the number of different run lengths.

Nonlimiting aspects of gray-level run-length based features include an angular second moment, a contrast, a correlation, a sum of squares, a variance, an inverse difference moment, a sum average, a sum variance, a sum entropy, a entropy, a difference variance, a difference entropy, an information measure of correlation 1, and an information measure of correlation 2. Computation of such features may be accomplished according to methodology well-recognized by those with skill in the relevant field.

For example, gray level non-uniformity may be determined according to the following equation 11:

$$GLN = \frac{\sum_{i=1}^{N_g}\left[\sum_{j=1}^{N_r} p(i,j|\theta)\right]^2}{\sum_{i=1}^{N_g}\sum_{j=1}^{N_r} p(i,j|\theta)}$$ Eq. 11

Run length non-uniformity may be determined according to the following equation 12:

$$RLN = \frac{\sum_{j=1}^{N_r}\left[\sum_{i=1}^{N_g} p(i,j|\theta)\right]^2}{\sum_{i=1}^{N_g}\sum_{j=1}^{N_r} p(i,j|\theta)}$$ Eq. 12

Run percentage may be determined according to the following equation 13:

$$RP = \sum_{i=1}^{N_g}\sum_{j=1}^{N_r} \frac{p(i,j|\theta)}{N_p}$$ Eq. 13

Long run emphasis may be determined according to the following equation 14:

$$LRE = \frac{\sum_{i=1}^{N_g}\sum_{j=1}^{N_r} j^2 p(i,j|\theta)}{\sum_{i=1}^{N_g}\sum_{j=1}^{N_r} p(i,j|\theta)}$$ Eq. 14

Location features are defined relative to the surface of the lung and are computed at each location $C_{ijk}$ within an HRCT scan or series of scans through a lung. Examples of location features may include a normalized distance to the diaphragm, a normalized distance to the right side of the lung, a normalized distance to the posterior side of the lung, a distance to lung surface, a distance to the right side of the lung, a distance to the left side of the lung, a distance to the anterior side of the lung, a distance to the posterior side of the lung, a distance to the diaphragm, and a distance to the lung apex. Computation of such features may be accomplished according to methodology well-recognized by those with skill in the relevant field.

For example, $k_N$ may be HRCT lung slices in a lung segmentation closest to the head and let $k_D$ may be HRCT lung slices in a lung segmentation closest to the diaphragm (which is also further way from the head). $i_R$ may be slices furthest on the right side of a subject and let $k_L$ may be slices on the far left side. $j_P$ may be the slices furthest on the posterior side of the lung and $j_A$ may be slices furthest on the anterior side. Normalized distance to the diaphragm may be determined in accordance with the following equation 15:

$$NDD=(k_D-k)/(k_D-k_N)$$ Eq. 15

Normalized distance to the right side of the lung may be determined in accordance with the following equation 16:

$$NDR=(i_R-i)/(i_R-i_L)$$ Eq. 16

Normalized distance to the posterior side of the lung may be determined in accordance with the following equation 17:

$$NDP=(j_P-j)/(j_P-i_A)$$ Eq. 17

In a further aspect of the method disclosed herein, referring to FIG. 1, extracted features are selected 130 for their importance in differentiating between UIP and non-UIP voxels. Feature selection may reduce the dimensionality of data and avoid what is known as the curse of dimensionality which may cause overfitting when large numbers of features are considered but only a few data samples are available. In one non-limiting example, to select features, feature importance provided by a random forest classifier may be combined with natural clustering via affinity propagation. Use of a random forest classifier and affinity propagation in machine learning and how to apply them to processing features of data are well understood by skilled artisans and their application to features extracted in accordance with the present invention would be envisaged, on the basis of the present disclosure, by skilled artisans. See Breiman, 2001, Machine Learning, 455-32; Dueck and Frey, "Non-metric affinity propagation for unsupervised image categorization," in Computer Vision, 2007. ICCV 2007. IEEE 11th International Conference on. IEEE, 2007, pp. 1-8.

To obtain the feature importance, a random forest classifier in a 10 fold cross-validation setting, i.e. 90% of the data, may be used for training; 10% for validation. Each cross-validation run may be trained with a different 2% random selection of pixels, and may provide a ranking for features. Multiple (e.g., 10-30) cross-validation trainings may be run to obtain an averaged importance of features. Moreover, affinity propagation clusters features based on their cross-correlations. By combining ranking obtained from a random forest classifier and affinity propagation correlations, important uncorrelated features may be retained. Two features may be considered redundant if they have a high cross-correlation, i.e., a cross-correlation above a threshold level. For example, two features may be considered redundant if their correlation is >0.8, >0.7, >0.6, or >0.5 computed on 2% of pixels. Among two correlated features, one that has a higher importance in the random forest classification may be retained, and the other feature discarded as the less informative of the two features. Only a subset of features (n<N) may selected. n<20 features may be found sufficient to capture the variability in HRCT lung scan data.

Referring again to FIG. 1, in accordance with the method disclosed herein, selected features may be used to create a model 140 for identifying probabilistic determinations of UIP tissue from HRCT lung scans. n selected features may be used to train a model in a machine learning paradigm. A random forest classifier may be used to construct a predictive model, according to methods well-known to those of skill in the relevant field. Following model construction by such training 140, the model may be used to evaluate other HRCT lung scans for identification of voxels therein that may signify the presence or absence of UIP tissue. A probability map may be created 150, applying the trained model 140 on voxels of a subject's HRCT lung scan, to signifying whether given voxels within the scan or series of scans throughout the subject's lungs, represents location of UIP diseased tissue.

In accordance with one embodiment of a method disclosed herein, textural features may be extracted automatically by a computer processor capable of performing a high number of calculations on data representing a series of lung HRCT scans. Imaging files may be obtained by scanning a subject in CT scanner. Resulting imaging files may be stored on a storage medium connected to or within a computer for processing of HRCT images (including labeling portions of scans, extracting and selecting features, and constructing a predictive model for reviewing HRCT scans and a probability map of a scan applying such predictive modeling) by an associated computer processor. In this embodiment, computer processing of features of HRCT scan data as disclosed herein represents functional improvements to HRCT technology. One function of HRCT is to provide visualizable computerized images of internal organs and potential diseased states. Automated processing of such computerized images in accordance with the method disclosed herein improves this functionality by enhancing the ability of representation of states of internal organs to be presented via HRCT.

In many if not most instances, automated computer processing of HRCT scans by a computer in accordance with the present disclosure provides improvements to HRCT scan functionality that would not be possible without assistance of computer hardware. Manual calculation of numerous textural feature characteristics for voxels throughout a scan or series of scans may, in many cases, exceed the lifespan of a subject whose scan or scans are being reviewed. Similarly, a process of generating a predictive model as disclosed herein, is a computerized process involving machine learning processes and represents an improvement in computerized analysis of HRCT scans, in that, for example, it includes computer learning of features in development of a predictive model.

EXAMPLES

The following examples are presented to further describe techniques in accordance with the method disclosed herein, but should not be read as limiting, because variations still within the scope of embodiments of the present invention will be apparent to those skilled in the art.

In an example, data from two independent institutions were used. These data are characterized in Table 1, below, in which PF stands for Pulmonary Fibrosis, HP stands for Hypersensitivity Pneumonitis; and NSIP stands for Non-specific interstitial pneumonia:

TABLE 1

Cohort characteristics

| Cohort | Training Set | Testing set | In-plane resolution | Slice thickness | Slice spacing | Labels |
|---|---|---|---|---|---|---|
| C1 | 46 | 6 | <1 mm | <2 mm | 1-10 mm | PF, HP, NSIP |
| C2 | — | 16 | <1 mm | <2 mm | 10 mm | UIP, Non-UIP |

Data and images for cohort C1 were obtained from a database available online, available at http://medgift.hevs.ch/silverstripe/index.php/team/adrien-depeursinge/multimedia-database-of-interstitial-lung-diseases/. Two expert radiologists annotated numerous regions of interest for 17 patterns in 14 diagnoses cohort C1. See Depeursinge et al. (2012), Comput. Med. Imaging Gr. 36:227-238.

Data and images for cohort C2 included histologic diagnosis of UIP and non-UIP conditions along with expert-drawn UIP and non-UIP regions of interest on HRCT. See Kim et al (2015), Lancet Respiratory Medicine, 3:473-482.

Subjects were excluded if (1) HRCT slice thickness was greater than 2 mm, (2) only a part of the lung was imaged and (3) if for C2, no clinical diagnosis was reported. This yield two final cohorts, C1 and C2 with N=52 and N=16 subjects, respectively.

To avoid over-fitting, all model training, parameter selection and cross-validation was performed on N=46 subjects from C1 (i.e. approximately 90% of N=52). Cohort C2 and 6 randomly chosen subjects from C1 (i.e. approximately 10%), were kept aside and reserved for testing and evaluation only.

To ensure reliable learning, the training cohort was selected to include conclusive honeycomb patterns in the UIP and conclusive non-honeycombing patterns in the non-UIP class, with the goal of avoiding patterns that appeared in both the UIP and the non-UIP groups. Since data in cohort C1 did not include a confirmed histological UIP versus non-UIP diagnosis, the 17 patterns outlined in C1 were mapped into UIP and Non-UIP classes based on the 14 available ILD labels. See Depeursinge et al. (2012), Comput. Med. Imaging Gr. 36:227-238. Specifically, patterns that were labeled as Pulmonary Fibrosis (PF) were included in the UIP group, while those that were PF-negative were included in the non-UIP group. Further, subjects with Hypersensitivity Pneumonitis (HP) may have a histology UIP pattern. Thus HP subjects with radiologist annotated UIP-related patterns were considered to be UIP, while the rest of the HP subjects (without UIP patterns) were included in the non-UIP group.

Regions of interest outlined by the experts on C1 were considered during the training, while the testing and validations was performed using the entire lung, either automatically segmented (using Lung VCAR, GE Healthcare) with manual corrections or as provided with the public dataset.

A total of N=71 texture features were computed for each voxel in the region of interest. The texture features were computed in a window 5 or 10 mm around the voxel and were computed in 2 dimensional space on axial planes, due to the large spacing (10 mm) between the slices. Considered were first and second order statistics, Haralick features extracted from co-occurrence matrices, Gray level run length, and localization features, e.g. the distance to the lung surface and distance to the diaphragm normalized by the size of the lung, as described above.

Figure 2:
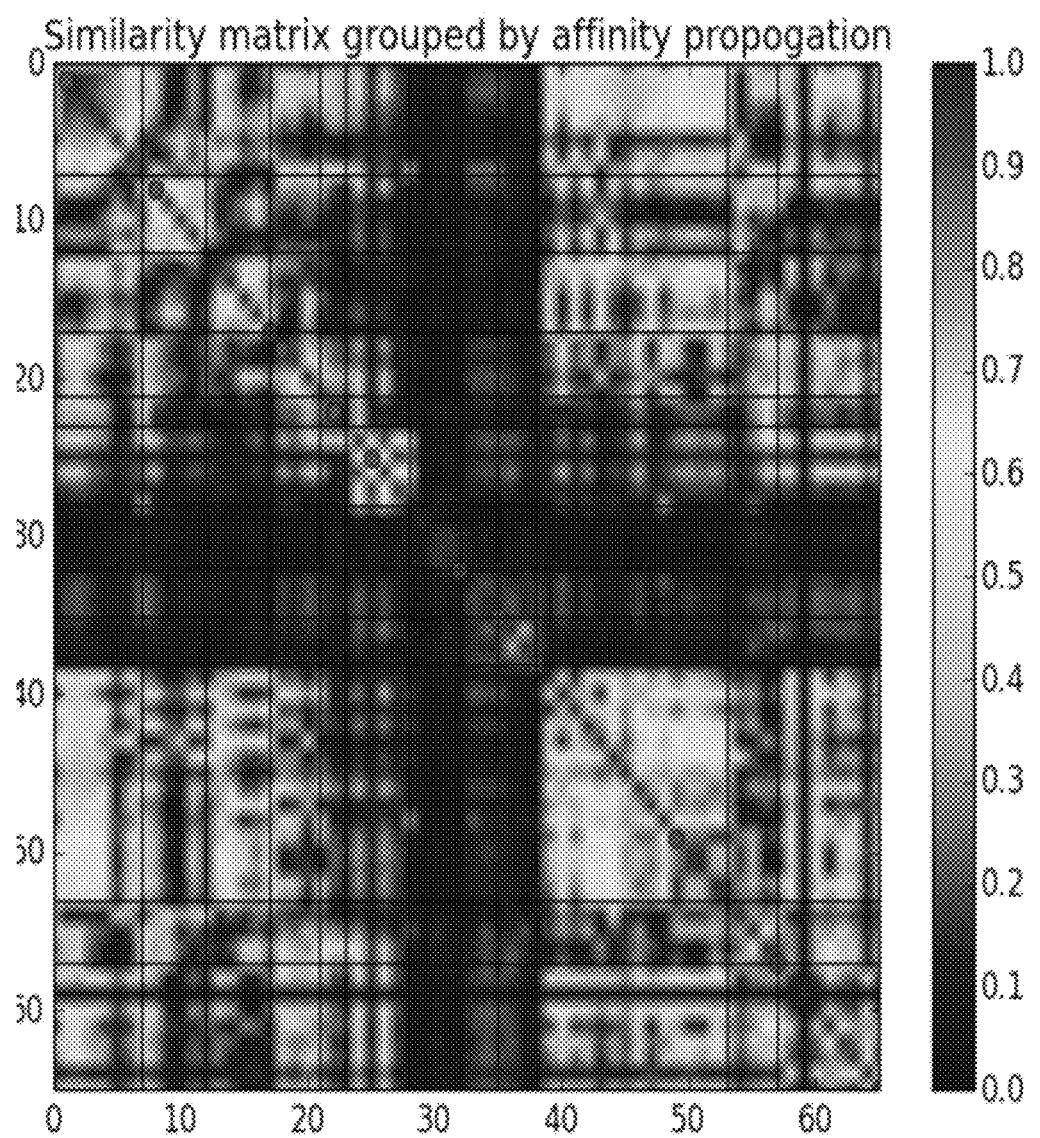
FIG. 2 is an illustration of one example of a heat map showing a natural clustering of features for use in selecting features to use in a diagnostic evaluation of UIP in accordance with the present invention.

Features selected to be strongly dependent on the outcome (i.e. target classification labels) while simultaneously being independent from each other yield enhanced classification performance. To achieve this, features were selected by combining Affinity Propagation (AP) and Random Forests (RF) to retain a small subset of meaningful features with low redundancy, in accordance with methodology described above. Given N candidate features, a corresponding N×N matrix of pair-wise cross-correlations was used as the similarity measure to find feature clusters showing high intra-cluster similarity and low inter-cluster similarity using AP. FIG. 2 shows a resulting cross-correlation between features grouped by cluster membership. Columns and rows represent features grouped by AP cluster membership, while the color-coded matrix values represent the cross-correlation between features.

Figure 3:
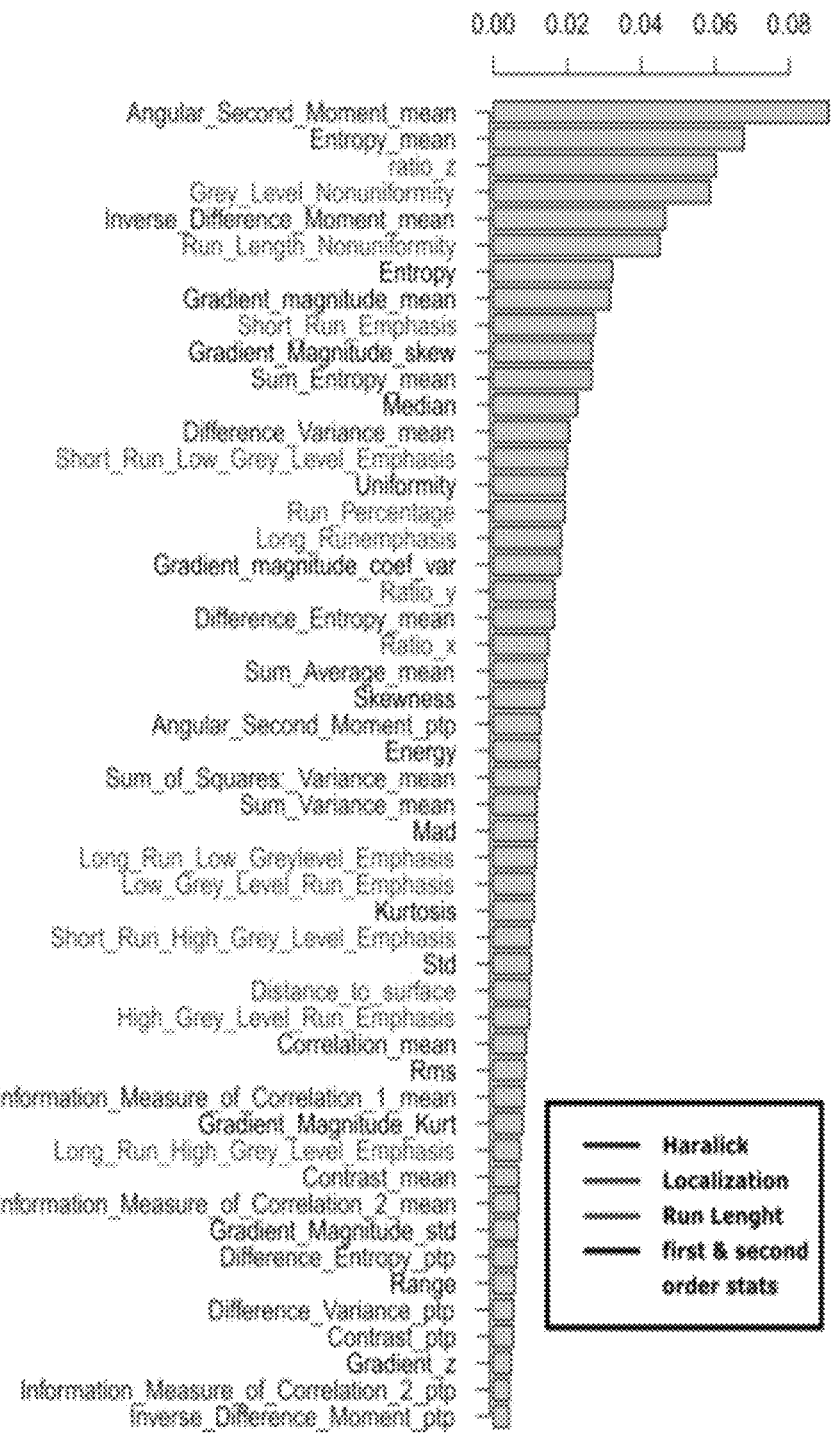
FIG. 3 is an illustration of one example of a rank of importance of extracted features of HRCT lung scans for selecting features to use in a diagnostic evaluation of UIP in accordance with the present invention.

In addition, the influence of each candidate feature on accurate UIP/non-UIP classification was estimated by using random forests. An RF classifier was trained in a 10 fold cross-validation setting, yielding 30 classifier runs with corresponding 'gini importance' values for each candidate feature. See Breiman, L., et al.: Classification and Regression Trees. Taylor and Francis (1984). A final feature influence was estimated by averaging the gini importance over all classifier runs. As shown in FIG. 3, features with high average importance were considered highly influential. In this example, the average accuracy of the classifier during training was 0.79±0.15, while the area under the curve (AUC) was 0.82±0.15.

To combine the benefits of AP and RF, pairs of features with greater than 0.8 within-cluster correlation were treated as highly dependent. Consequently redundancy was reduced by removing the feature with the lower average gini-importance from the feature set. This process was repeated until a small group of n<<N highly influential features with low cross-correlation values was left. To reduce computation time, feature selection was performed using candidate features generated only at a randomly selected subset of 2% of the voxels in the training set. The final set contained as many as n=21 influential features.

Having selected the n most influential features with minimal interdependence, an RF classifier (300 trees, minimum sample split of 4 and minimum sample leaf of 2) was trained and cross-validated using 10 folds on the N=46 training set from C1. To reduce computation time, training utilized only 20% of randomly chosen voxels from each subject in the training set. The final classifier output was a voxel-wise probability map $\{P_{UIP}(x)\}$, $x \in R^3$ predicting UIP versus non-UIP status at each voxel location within the lung. A threshold of 0.5 was applied to binarize the probability map into UIP ($\{x: P_{UIP}(x) > 0.5\}$) versus non-UIP classes. In other examples, lower or higher thresholds may be used, depending on the a preferred model sensitivity and selectivity.

Figure 4:
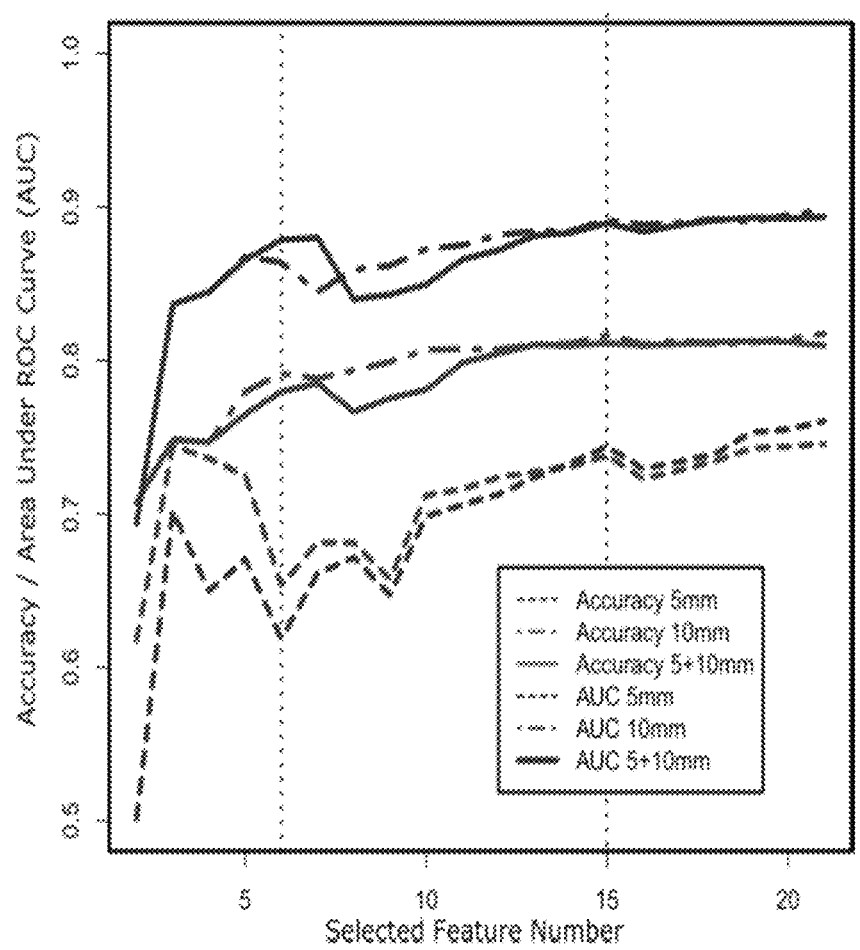
FIG. 4 is a graphical representation depicting one example of accuracy and area under the curve (AUC) for various combinations of features that may be used in a diagnostic evaluation of UIP in accordance with the present invention.
Figure 5:
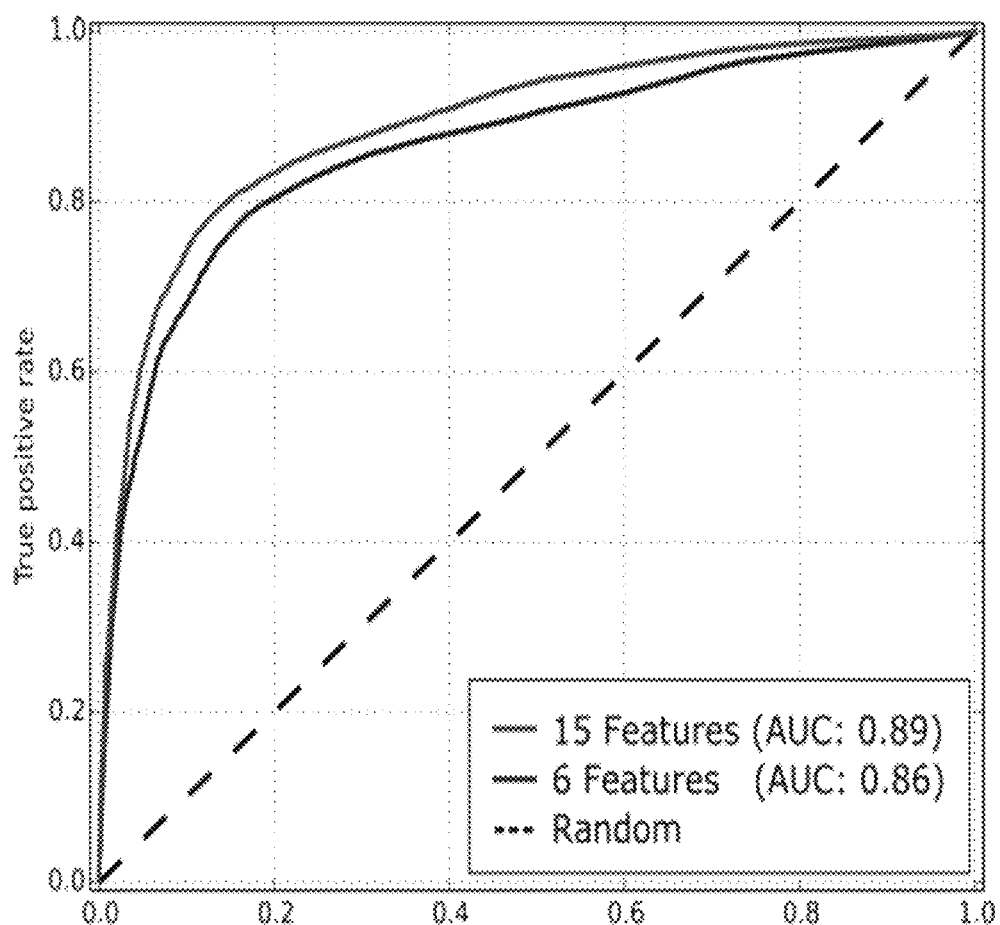
FIG. 5 is a graphical representation of receiver-operator curves (ROC) for 6 and 15 features that may be used in a diagnostic evaluation of UIP in accordance with the present invention.

To study incremental effect of features and widow-sizes on classification performance, a series of 20 random forests, $\{RF_i\}$, i=2, 3 . . . , n=21, was evaluated in the training set using 10 fold cross validation. Each RF used progressively more features, i.e. $RF_i$ used only the top i most influential features. FIG. 4 summaries the evaluation, depicting accuracy and AUC for various combinations of features. In this example, there was a considered improvement in AUC and accuracy when more than 3 features were used in the prediction. For more than 10 features, only minimal improvements may be observed with the addition of each feature. Based on this results predictive models were further evaluated using either 6 or 15 features computed in a window size of 10 mm. FIG. 5 shows the receiver-operator curve (ROC) for 6 and 15 features, indicating on only 0.03 in AUC improvement when going from 6 to 15 features. Consequently, for this example, all final model testing was restricted to $RF_6$ and $RF_{15}$ with a window-size of 10 mm.

The performance of the final two classifiers $RF_6$ and $RF_{15}$ trained on the entire training set N=46 from C1 using the top 6 and top 15 features was evaluated on the hitherto unseen test-sets: N=6 for C1 and all of cohort C2. A voxel-wise probability map $\{P_{UIP}(x)\}$, $x \in R^3$ from each classifier was binarized by applying a threshold of 0.5 to produce a map of UIP ($\{x: P_{UIP}(x) > 0.5\}$) versus non-UIP classes.

Classifier performance was quantified by computing the accuracy defined as the percentage of correct prediction for both classes, and area under the ROC curve (AUC) for test cases where ground-truth UIP versus non-UIP regions of interest were available. Precision, sensitivity, specificity and the F 1 score were also measured. This approach demonstrated high accuracy (>0.82) and specificity (>0.82) in both cohorts, as demonstrated in Table 2, below.

TABLE 2

Evaluation of predictive models for independent cohorts.

| Testing sets | Model Type | Accuracy | Precision | Sensitivity | Specificity | F1 |
|---|---|---|---|---|---|---|
| C1 | $RF_6$ | 0.82 | 0.51 | 0.84 | 0.82 | 0.63 |
| N = 6 | $RF_{15}$ | 0.85 | 0.55 | 0.85 | 0.85 | 0.67 |
| C2 | $RF_6$ | 0.84 | 0.65 | 0.45 | 0.94 | 0.53 |
| N = 16 | $RF_{15}$ | 0.85 | 0.73 | 0.47 | 0.95 | 0.57 |

Figure 6:
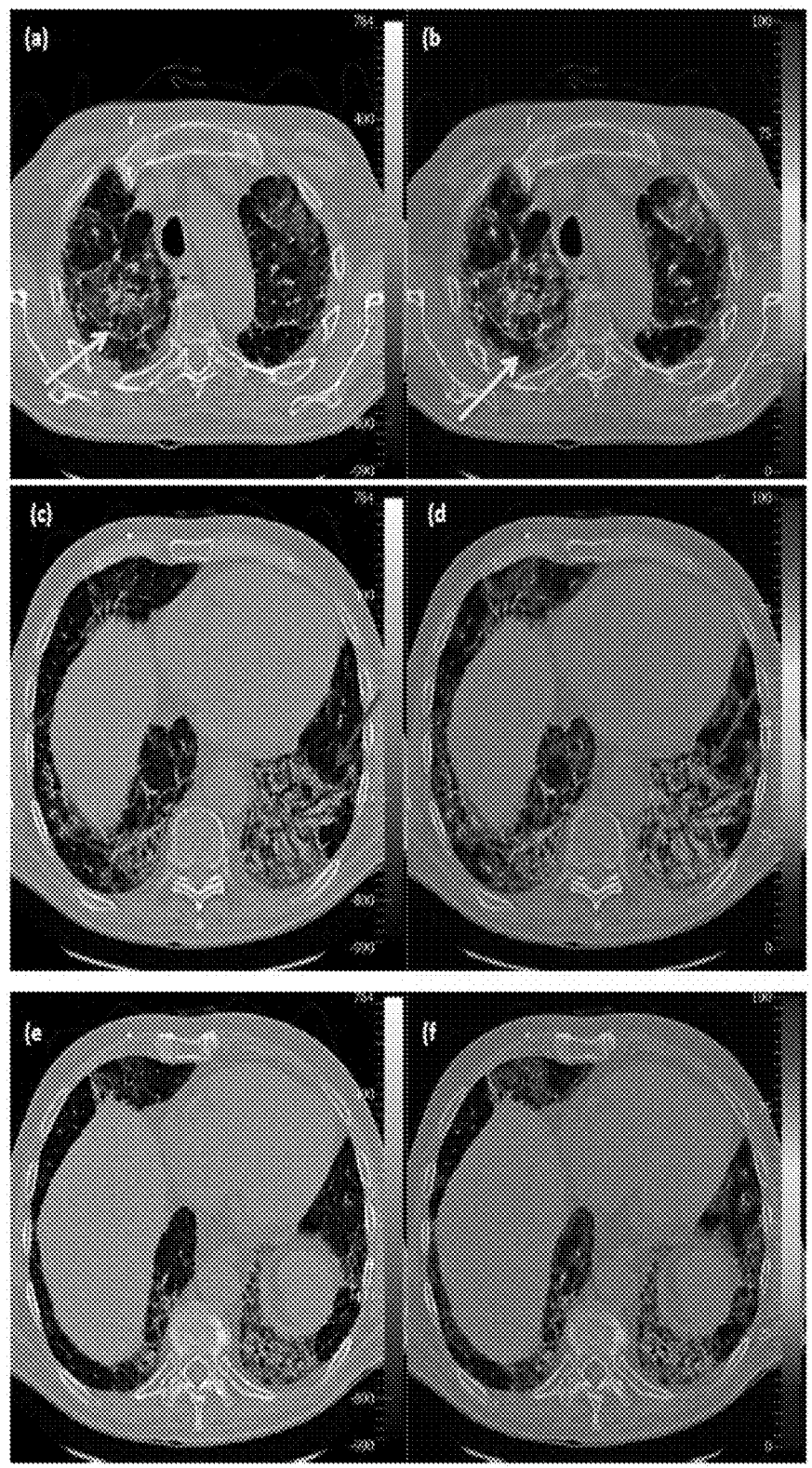
FIG. 6 is a graphical representation of a prediction map for UIP on HRCT scans in accordance with the present invention.
Figure 7:
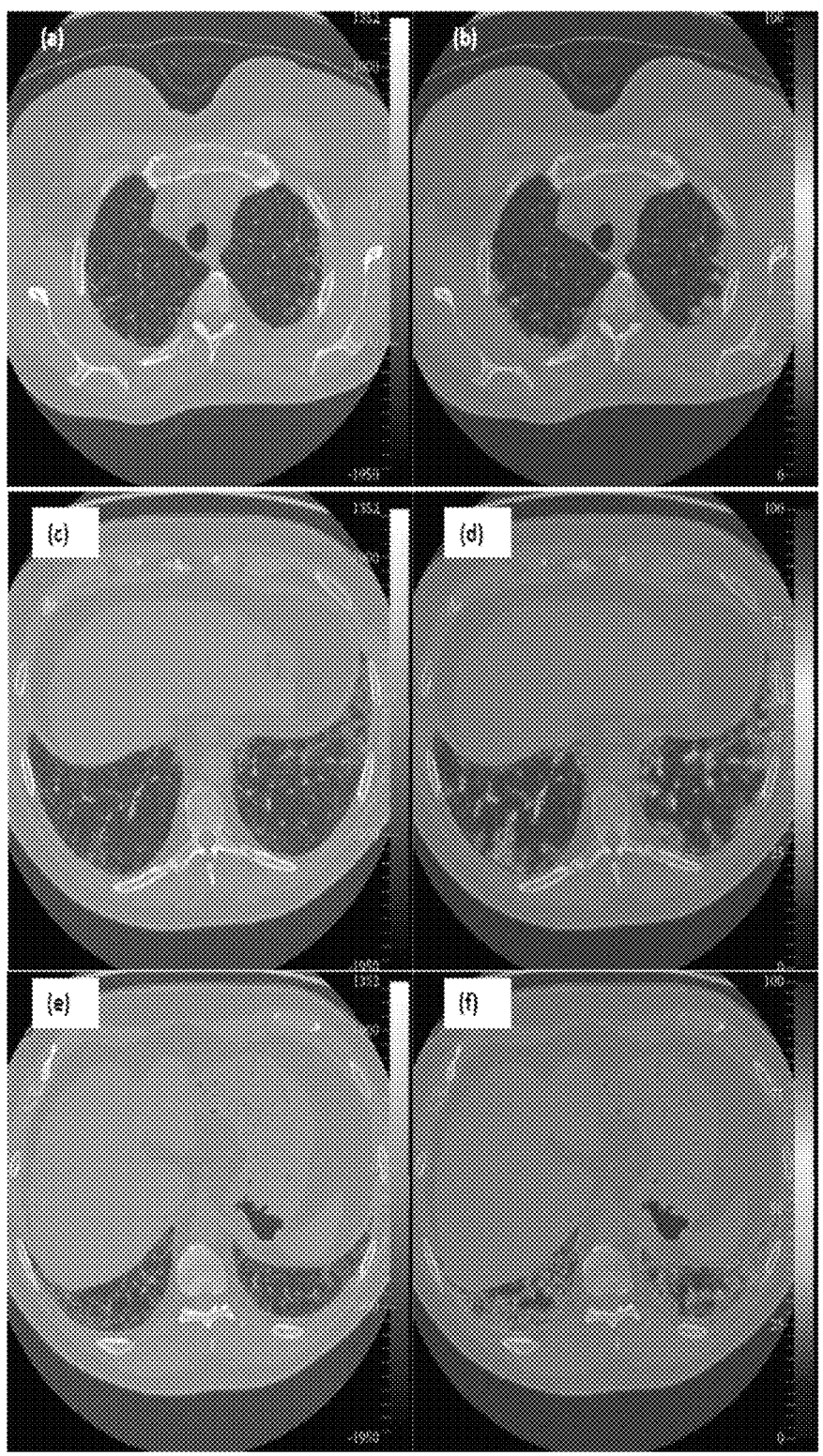
FIG. 7 is a graphical representation of UIP prediction in a subject with histological confirmed UIP in accordance with the present invention.
Figure 8:
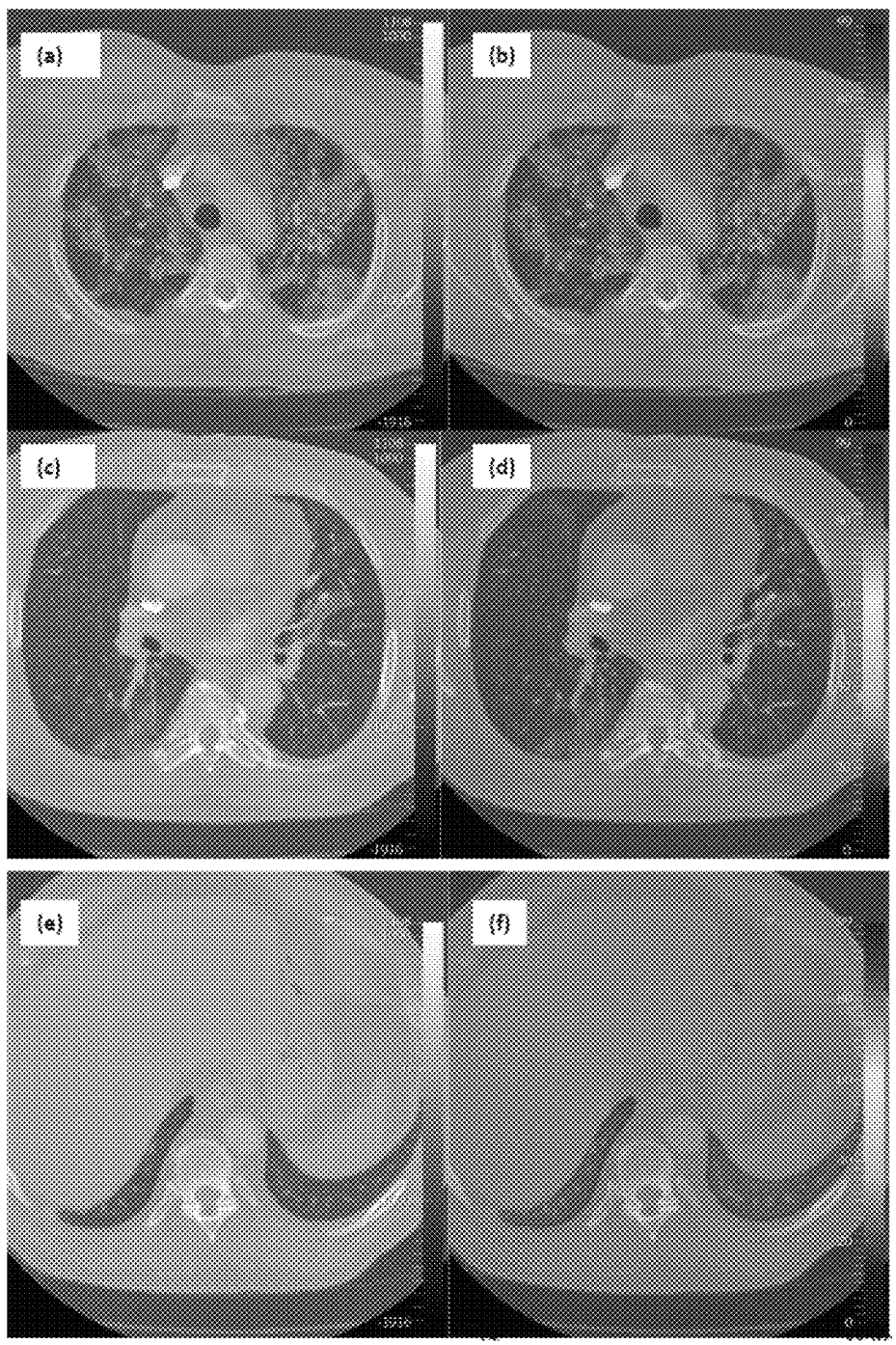
FIG. 8 is a graphical representation of UIP prediction in a subject with a non-UIP diagnosis.

FIGS. 6-8 show per-voxel UIP predictions in a C1 subject (FIG. 6) and two C2 subjects with (FIG. 7) or without (FIG. 8) UIP confirmed histologically. Per-voxel predictions show consistent visual representations, correlating high UIP probabilities with honeycomb patterns and also capture other UIP patterns such as reticulation.

What is claimed is:

1. A method for creating a diagnostic evaluation for usual interstitial pneumonia (UIP) comprising:
    obtaining a first plurality of series of high resolution computed tomography (HRCT) slices of a plurality of subjects' lungs wherein some voxels of some of the first plurality of series indicate the presence of UIP;
    obtaining an identification of UIP voxels in at least some of the plurality of series and an identification of non-UIP voxels in at least some of the plurality of series wherein the UIP voxels represent the presence of UIP in an area of the lung represented by the UIP voxels and non-UIP voxels represent the absence of UIP in an area of the lung represented by the non-UIP voxels;
    extracting a first plurality of features from said UIP voxels and said non-UIP voxels, wherein extracting comprises measuring each of the first plurality of features as exhibited by the UIP voxels and by the non-UIP voxels and the first plurality of features comprise first-order statistics, second-order statistics, gray level co-occurrence matrix, gray level run-length matrix, and location features;
    selecting features wherein selecting comprises performing a first classifier to obtain a rank of importance for each of the plurality of features in which a higher-ranked feature provides a measure that is more accurate in differentiating UIP voxels from non-UIP voxels than is a lower-ranked feature, and eliminating one or more redundant features wherein a redundant feature comprises a feature whose measure as exhibited by voxels is highly correlated with the measure of another feature as exhibited by voxels having a higher rank of importance than the redundant feature; and
    constructing a predictive model wherein constructing comprises obtaining a second plurality of series of HRCT slices of subjects' lungs wherein some voxels of some of the plurality of series indicate the presence of UIP and training a number of the subset of features to provide a probability that a voxel signifies the presence of UIP by performing a second classifier on the number of the subset of features.

2. A method according to claim 1, wherein the first-order statistics comprise one or more of a mean, a median, a standard deviation, an energy, a skewness, an intensity, a root mean square a deviation, a uniformity, a maximum, a range, a minimum, an entropy, a mean absolute deviation, a variance, and a kurtosis.

3. A method according to claim 1, wherein the second-order statistics comprise one or more of a gradient z, a gradient y, a gradient x, a gradient magnitude, a gradient magnitude mean, a gradient magnitude standard deviation, a gradient magnitude skewness, a gradient magnitude kurtosis, and a gradient magnitude coefficient of variation.

4. A method according to claim 1, wherein the gray level co-occurrence matrix comprises one or more of an angular second moment, a contrast, a correlation, a sum of squares, a variance, an inverse difference moment, a sum average, a sum variance, a sum entropy, a entropy, a difference variance, a difference entropy, an information measure of correlation 1, and an information measure of correlation 2.

5. A method according to claim 1, wherein the gray level run-length matrix comprises one or more of a short run emphasis, long run emphasis, low grey level run emphasis, high grey level run emphasis, short run low grey level emphasis, short run high grey level emphasis, and a long run low grey level.

6. A method according to claim 1, wherein the location features comprise one or more of a normalized distance to the diaphragm, a normalized distance to the right side of the lung, a normalized distance to the posterior side of the lung, a distance to lung surface, a distance to the right side of the lung, a distance to the left side of the lung, a distance to the anterior side of the lung, a distance to the posterior side of the lung, a distance to the diaphragm, and a distance to the lung apex.

7. A method according to claim 1, wherein the number of the subset of features is fifteen or less.

8. A method according to claim 7, wherein the subset of features comprise an angular second moment mean, a normalized distance from the diaphragm, a gray level nonuniformity, a run length nonuniformity, gradient magnitude skewness, a median, a normalized distance from the right side of the lung, an angular second moment peak-to-peak, a difference variance mean, a gradient magnitude coefficient of variation, an energy, a normalized distance from the posterior surface of the lung, a run percentage, a long run emphasis, and a skewness.

9. A method according to claim 7, wherein the number of the subset of features is six or less.

10. A method according to claim 9, wherein the subset of features comprises an angular second moment mean, a normalized distance from the diaphragm, a gray level nonuniformity, a run length nonuniformity, gradient magnitude skewness, and a median.

11. A method according to claim 1, wherein the measure of one feature as exhibited by voxels is highly correlated with the measure of another feature as exhibited by voxels when a coefficient of correlation between the measure of the one feature and the measure of the other feature is 0.8 or higher.

12. A method according to claim 1, wherein
the first-order statistics comprise one or more of a mean, a median, a standard deviation, an energy, a skewness, an intensity, a root mean square a deviation, a uniformity, a maximum, a range, a minimum, an entropy, a mean absolute deviation, a variance, and a kurtosis;
the second-order statistics comprise one or more of a gradient z, a gradient y, a gradient x, a gradient magnitude, a gradient magnitude mean, a gradient magnitude standard deviation, a gradient magnitude skewness, a gradient magnitude kurtosis, and a gradient magnitude coefficient of variation;
the gray level co-occurrence matrix comprises one or more of an angular second moment, a contrast, a correlation, a sum of squares, a variance, an inverse difference moment, a sum average, a sum variance, a sum entropy, a entropy, a difference variance, a difference entropy, an information measure of correlation 1, and an information measure of correlation 2;
the gray level run-length matrix comprises one or more of a short run emphasis, long run emphasis, low grey level run emphasis, high grey level run emphasis, short run low grey level emphasis, short run high grey level emphasis, and a long run low grey level; and
the location features comprise one or more of a normalized distance to the diaphragm, a normalized distance to the right side of the lung, a normalized distance to the posterior side of the lung, a distance to lung surface, a distance to the right side of the lung, a distance to the left side of the lung, a distance to the anterior side of the lung, a distance to the posterior side of the lung, a distance to the diaphragm, and a distance to the lung apex.

13. A method according to claim 12, wherein the measure of one feature as exhibited by voxels is highly correlated with the measure of another feature as exhibited by voxels when a coefficient of correlation between the measure of the one feature and the measure of the other feature is 0.8 or higher.

14. A method according to claim 12, wherein the number of the subset of features is six or less.

15. A method according to claim 14, wherein the subset of features comprise an angular second moment mean, a normalized distance from the diaphragm, a gray level nonuniformity, a run length nonuniformity, a gradient magnitude skewness, and a median.

16. A method according to claim 14, wherein the number of the subset of features is fifteen or less.

17. A method according to claim 16, wherein the subset of features comprises an angular second moment mean, a normalized distance from the diaphragm, a gray level nonuniformity, a run length nonuniformity, gradient magnitude skewness, a median, a normalized distance from the right side of the lung, an angular second moment peak-to-peak, a difference variance mean, a gradient magnitude coefficient of variation, an energy, a normalized distance from the posterior surface of the lung, a run percentage, a long run emphasis, and a skewness.

18. A method according to claim 1, wherein the first classifier is a random forest classifier.

19. A method according to claim 1, wherein eliminating one or more redundant features comprises performing affinity propagation.

20. A method for identifying the presence of UIP in a subject's lung comprising:
obtaining a diagnostic evaluation for UIP that was created with the method of claim 1,
obtaining a series of HRCT slices of the lungs of a subject; and
measuring, for voxels of the series, each of the number of the subset of features to provide a probability that a voxel signifies the presence of UIP.

* * * * *